(12) United States Patent
Kisela et al.

(10) Patent No.: US 10,054,558 B2
(45) Date of Patent: Aug. 21, 2018

(54) SYSTEM AND METHOD FOR TESTING THERMAL PROPERTIES OF A CONTAINER

(71) Applicant: Owens-Brockway Glass Container Inc., Perrysburg, OH (US)

(72) Inventors: David Kisela, Sylvania, OH (US); Jared Morello, Columbus, OH (US); Gary Myers, New Albany, OH (US); Daniel S. Sabo, Dublin, OH (US)

(73) Assignee: Owens-Brockway Glass Container Inc., Perrysburg, OH (US)

( * ) Notice: Subject to any disclaimer, the term of this patent is extended or adjusted under 35 U.S.C. 154(b) by 237 days.

(21) Appl. No.: 14/142,156

(22) Filed: Dec. 27, 2013

(65) Prior Publication Data

US 2015/0185172 A1 Jul. 2, 2015

(51) Int. Cl.
| | |
|---|---|
| *G01N 25/18* | (2006.01) |
| *G01N 25/72* | (2006.01) |
| *G01M 99/00* | (2011.01) |

(52) U.S. Cl.
CPC .......... *G01N 25/18* (2013.01); *G01M 99/002* (2013.01); *G01N 25/72* (2013.01)

(58) Field of Classification Search
CPC ...... G01N 25/18; G01N 25/72; G01M 99/002
USPC ............................................ 73/865.6; 374/44
See application file for complete search history.

(56) References Cited

U.S. PATENT DOCUMENTS

| | | | | |
|---|---|---|---|---|
| 3,424,231 A | * | 1/1969 | Truhan ................ | G01M 99/002 165/230 |
| 3,491,581 A | * | 1/1970 | Harlan ................ | G01N 25/486 374/12 |
| 3,695,093 A | * | 10/1972 | Hummel ................ | G01N 25/04 374/25 |
| 3,718,437 A | * | 2/1973 | Paloniemi .......... | G01N 25/4853 374/33 |
| 3,805,594 A | * | 4/1974 | Hayashi ................ | G01N 3/12 73/37 |
| 3,841,155 A | * | 10/1974 | Koehler ............... | G01N 25/486 374/33 |
| 3,894,424 A | * | 7/1975 | Taylor ..................... | G01N 3/12 134/152 |
| 3,895,514 A | * | 7/1975 | Northup .................. | G01N 3/12 73/49.4 |
| 4,090,394 A | * | 5/1978 | Herman .................. | G01N 3/12 73/37 |

(Continued)

FOREIGN PATENT DOCUMENTS

DE 29621935 3/1997

OTHER PUBLICATIONS

PCT Search Report and Written Opinion, Int. Serial No. PCT/US2014/070357, Int. Filing Date: Dec. 15, 2014, Applicant: Owens-Brockway Glass Container Inc., dated Mar. 19, 2015

(Continued)

*Primary Examiner* — Harshad R Patel
*Assistant Examiner* — Tran M Tran (57) ABSTRACT

A container test system includes a test chamber in which a container may be located for testing, for instance, for assessing insulative properties of a container. In the test chamber, the outside of the container is thermally treated, temperature of the air outside the container is measured, and temperature of a liquid inside the container is measured. A related testing method is also disclosed.

27 Claims, 4 Drawing Sheets

(56) References Cited

U.S. PATENT DOCUMENTS

| | | | |
|---|---|---|---|
| 4,095,454 A * | 6/1978 | Fisher | G01M 99/002 374/43 |
| 4,148,223 A | 4/1979 | Disinski | |
| 4,156,454 A * | 5/1979 | Skala | A47J 27/17 165/259 |
| 4,285,230 A * | 8/1981 | Hartness | G01N 3/12 73/37 |
| 4,304,119 A * | 12/1981 | Uchigaki | G01N 25/04 374/25 |
| 4,379,775 A * | 4/1983 | Brandstetr | G01N 25/4846 374/33 |
| 4,492,480 A * | 1/1985 | Wadso | G01K 1/16 165/169 |
| 4,575,257 A * | 3/1986 | Ogura | G01N 25/00 126/285 B |
| 4,602,503 A * | 7/1986 | Hile | G01R 31/2862 73/865.6 |
| H229 H * | 3/1987 | Phillips | 165/48.1 |
| 4,667,506 A * | 5/1987 | Jenkins | G01M 3/3209 73/45.2 |
| 4,733,973 A * | 3/1988 | Machak | G01N 33/386 141/94 |
| 4,760,538 A * | 7/1988 | Bock | G01N 33/2811 374/24 |
| 4,854,726 A * | 8/1989 | Lesley | G01N 17/00 165/254 |
| 4,923,306 A * | 5/1990 | Fauske | G01K 17/00 165/11.1 |
| 4,998,582 A | 3/1991 | Fudono et al. | |
| 5,039,228 A | 8/1991 | Chalmers | |
| 5,141,329 A * | 8/1992 | Orlando | G01N 25/04 374/16 |
| 5,167,451 A * | 12/1992 | Muller | G01M 99/002 374/45 |
| 5,258,929 A * | 11/1993 | Tsuchida | G01N 25/18 374/44 |
| 5,282,682 A * | 2/1994 | Orlando | G01N 25/04 374/16 |
| 5,481,882 A * | 1/1996 | Watanabe | F25D 16/00 165/104.22 |
| 5,610,344 A | 3/1997 | Ueda et al. | |
| 5,773,730 A * | 6/1998 | McConnell | F24F 11/001 73/863.83 |
| 5,980,103 A * | 11/1999 | Ikuno | G01N 3/60 374/5 |
| 5,988,875 A * | 11/1999 | Gershfeld | G01N 25/4866 374/10 |
| 6,191,599 B1 * | 2/2001 | Stevens | G01R 31/2862 324/750.07 |
| 6,227,701 B1 * | 5/2001 | Wu | G01R 31/2849 374/45 |
| 6,501,290 B2 * | 12/2002 | Kvanvig | G01R 31/2875 324/750.09 |
| 6,511,372 B2 * | 1/2003 | Leeds | F24F 11/04 138/46 |
| 6,564,566 B2 * | 5/2003 | Kim | F25D 17/065 62/225 |
| 6,572,263 B1 * | 6/2003 | Refalo | G01K 17/04 374/31 |
| 6,925,872 B2 * | 8/2005 | Hadala | G01F 23/22 165/168 |
| 7,074,364 B2 * | 7/2006 | Jahn | B01J 19/0046 422/606 |
| 7,246,938 B2 * | 7/2007 | Ševčik | G01N 25/30 374/1 |
| 7,263,856 B2 * | 9/2007 | Choi | F25D 17/045 62/408 |
| 7,302,846 B2 * | 12/2007 | Hadala | G01F 23/22 73/290 R |
| 7,371,006 B2 * | 5/2008 | Schick | G01N 25/4866 374/10 |
| 7,407,631 B2 * | 8/2008 | Swon | B01F 11/0082 366/273 |
| 7,488,106 B2 * | 2/2009 | Brushwyler | G01K 17/00 374/31 |
| 7,543,479 B2 * | 6/2009 | Thomas | G01M 3/3263 73/37 |
| 8,359,906 B2 * | 1/2013 | Shimada | G01R 31/2874 73/73 |
| 8,393,234 B2 * | 3/2013 | Haefner | G01N 21/0332 73/863 |
| 8,479,597 B2 * | 7/2013 | Pickel | G01M 7/027 73/571 |
| 8,485,039 B2 * | 7/2013 | Provost | G01M 7/02 73/663 |
| 8,506,160 B2 * | 8/2013 | Johnson | G01M 99/002 374/109 |
| 8,567,268 B2 * | 10/2013 | Sun | G05D 22/02 73/431 |
| 8,616,063 B2 * | 12/2013 | Provost | G01M 99/002 73/663 |
| 8,628,235 B2 * | 1/2014 | Davies | G01N 25/72 374/109 |
| 8,668,380 B2 * | 3/2014 | Schenker | G01K 17/04 374/31 |
| 8,763,480 B2 * | 7/2014 | Shimada | G01N 25/68 73/73 |
| 8,783,117 B2 * | 7/2014 | Chang | F04D 27/001 73/861.85 |
| 9,506,670 B2 * | 11/2016 | Vanthournout | F24D 19/1063 |
| 2003/0146224 A1 * | 8/2003 | Fujii | A47J 41/022 220/592.27 |
| 2005/0145048 A1 | 7/2005 | Moir et al. | |
| 2006/0064257 A1 * | 3/2006 | Pennington | G01F 17/00 702/50 |
| 2007/0249277 A1 | 10/2007 | Chou | |
| 2010/0264107 A1 | 10/2010 | Lonsway et al. | |
| 2011/0172807 A1 * | 7/2011 | Merrow | G11B 17/225 700/213 |
| 2012/0000878 A1 | 1/2012 | Reisig | |
| 2012/0011859 A1 * | 1/2012 | Black | F25D 19/00 62/48.1 |
| 2012/0291627 A1 * | 11/2012 | Tom | F17C 1/00 95/8 |

OTHER PUBLICATIONS

S. Kamiya, et al., "Thermal Test of the Insulation Structure for LH2 Tank by Using the Large Experimental Apparatus", Cryogenics, Elsevier, Kidlington, GB, vol. 40, No. 11, Jan. 1, 2000.

Chinese First Office Action, Patent Application No. 201480071264.4, Applicant: Owens-Brockway Glass Container Inc., Title: Container Test System, dated Nov. 3, 2017.

Chile Examiners Report, Serial No. 201601639, Applicant: Owens-Brockway Glass Container Inc., dated May 15, 2018.

* cited by examiner

SYSTEM AND METHOD FOR TESTING THERMAL PROPERTIES OF A CONTAINER

The present disclosure is directed to containers and, more particularly, to measurement of fluid temperature in containers.

BACKGROUND AND SUMMARY OF THE DISCLOSURE

A general object of the present disclosure, in accordance with one aspect of the disclosure, is to provide a method and system to measure change in temperature of liquid in a container, for example, to assess insulation performance of the container.

The present disclosure embodies a number of aspects that can be implemented separately from or in combination with each other.

A container test system in accordance with one aspect of the disclosure includes a test chamber including an air inlet, an air outlet downstream of the air inlet, and a container location between the inlet and the outlet. The system also includes a climate controller located upstream of the air outlet, to control the climate in the test chamber, and at least one air temperature sensor located adjacent to the container location.

In accordance with another aspect of the disclosure, there is provided a method of assessing insulative properties of a container. The method includes positioning the container in a test chamber, and filling the container with cooled liquid by delivering the cooled liquid from the cooled liquid source until the cooled liquid reaches a fill level in the container. The method further includes thermally treating the outside of the container within the test chamber, measuring temperature of the air outside the container, and measuring temperature of the liquid inside the container.

BRIEF DESCRIPTION OF THE DRAWINGS

The disclosure, together with additional objects, features, advantages and aspects thereof, will be best understood from the following description, the appended claims and the accompanying drawings, in which:

DETAILED DESCRIPTION

Figure 1:
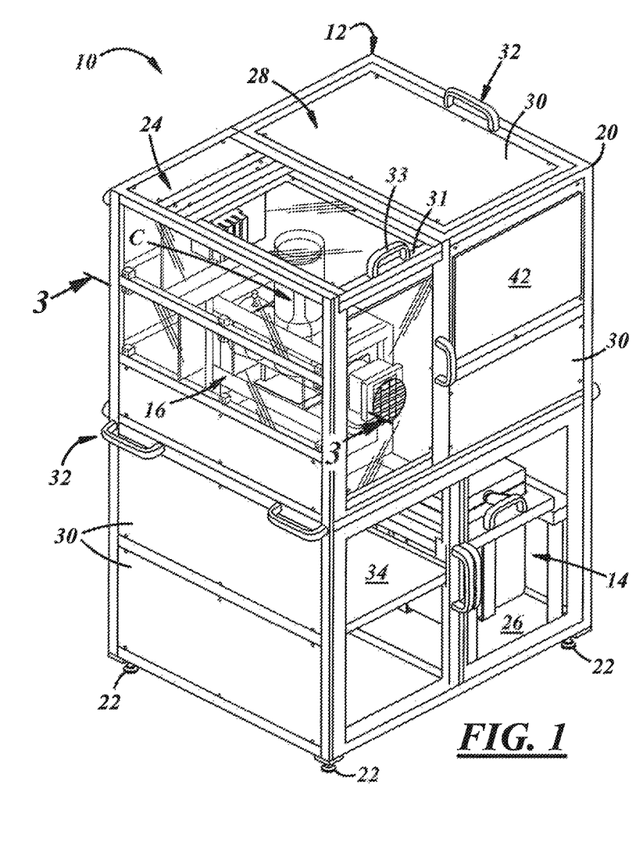
FIG. 1 is an upper, left side, perspective view of a container test stand in accordance with an illustrative embodiment of the present disclosure.
Figure 2:
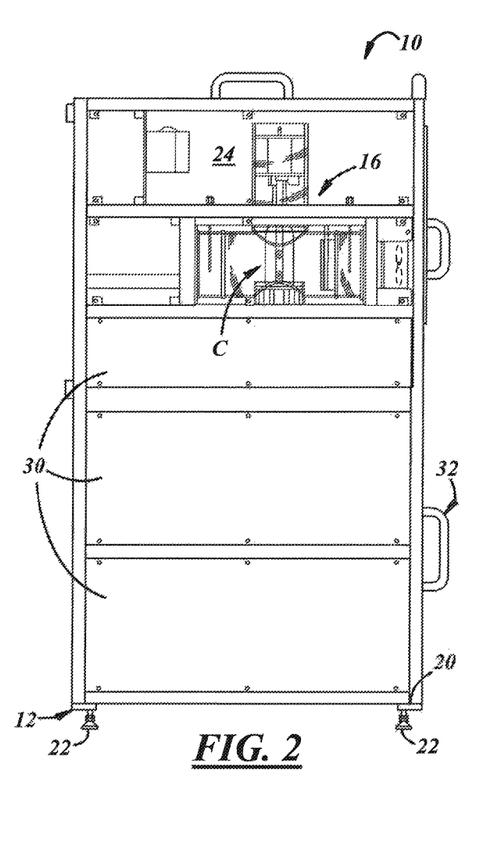
FIG. 2 is a left side view of the test stand of FIG. 1.

Referring generally to FIGS. 1-4, there is illustrated a container test system 10 to assess insulative performance of a container C (FIGS. 1-2). In general, the system 10 may include a support structure 12 to support other portions of the system 10, a source 14 (FIG. 3) of cooled liquid for filling the container C, a test assembly 16 in which the container C is tested and in fluid communication with the cooled liquid source 14, and various mechanical and electrical utilities 18 (FIG. 4) coupled to the test assembly 16 and/or to the cooled liquid source 14 to facilitate testing of the container C. The system 10 may be coupled to external utility sources (not separately shown), for example, a generator or utility power supply, telecommunication services, water supply, waste drain, and any other suitable utility sources. Also, the system 10 may include any suitable fluid conduit, cables, wires, valves, check valves, or any other suitable elements that may not be illustrated in the drawings for clarity.

Figure 4:
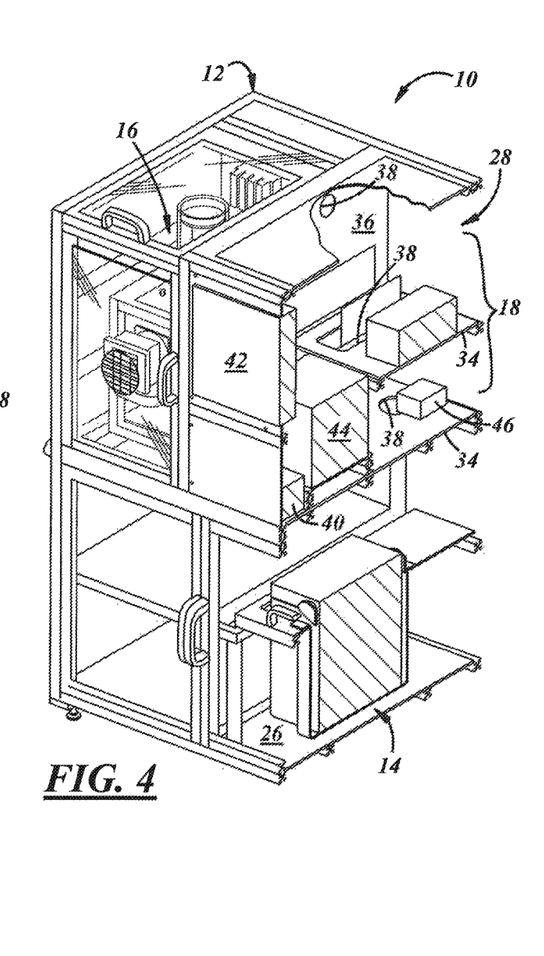
FIG. 4 is a fragmentary perspective view of the test stand of FIG. 1, similar to the view of FIG. 3.

The support structure 12 may include framework or a chassis 20, and adjustable feet 22 on which the chassis 20 is carried. The support structure 12 may include a test bay 24 for testing the container C, a cooler bay 26 that may be located below and to the side of the test bay 24 for carrying coolant, and a mechanical and electrical utility bay 28 above the cooler bay 26 for carrying the various mechanical and electrical sub-systems to support the test assembly 16. The support structure 12 also may include exterior panels 30 carried by the chassis 20, handles 32 for handling the chassis 20 and/or the panels 30, and bracketry/shelving 34 to carry various portions of the system 10. For example, a container access panel 31 may include a handle 33 at one end for removing the panel 31 and gaining access to the test bay 24. Also, as shown in FIG. 4, the support structure 12 may include internal panels or walls 36, for instance, to separate the utility bay 28 from the test bay 24. The structure 12 also may include various ventilation apertures 38 in the walls 36 and/or the shelving 34.

Figure 3:
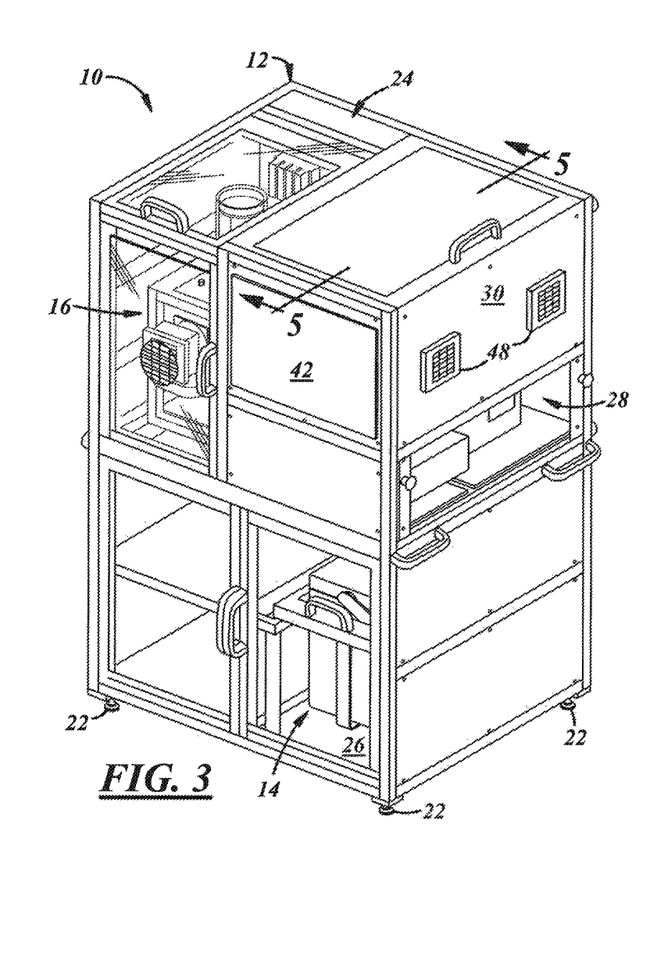
FIG. 3 is an upper, right side, perspective view of the test stand of FIG. 1.

With reference to FIG. 3, the cooled liquid source 14 may include a cooler to carry a cooled liquid used in carrying out testing. In one embodiment, the cooled liquid may include water and, more specifically, may include a solvent mixture. For example, the cooled liquid may include a mixture of 95% water and 5% isopropyl alcohol. In other embodiments, the cooled liquid may include beer, wine, liquor, or any other suitable liquid. The source 14 may carry a coolant to cool the liquid. For instance, the source 14 may carry the liquid in a manner surrounded by the coolant, or vice-versa, with any suitable wall(s), tubing, or any other suitable barrier(s) therebetween. In one embodiment, the coolant may include ice. For example, the coolant may include ice and salt, or a salt/ice bath. In other embodiments, the coolant may include ice water, dry ice, or any other suitable coolant. In still other embodiments, the coolant may include a refrigerant, wherein the source 14 may include a refrigeration apparatus. A cooled liquid temperature sensor (not separately shown) may be coupled to the cooled liquid source 14 to measure the temperature of the cooled liquid and may be communicated to the utilities 18.

In any case, the storage temperature of the cooled liquid at the source 14 may range from −10 to 50 degrees Celsius, and the operational temperature of the cooled liquid in the container C may range from 0 to 40 degrees Celsius. Preferably, the temperature of the cooled liquid in the source 14 may be below a desired test temperature of the cooled liquid in the container C, for example, 2 to 4 degrees Celsius below, to account for heat transfer during delivery therebetween. More specifically, a desired temperature of the cooled liquid at the source 14 for delivery into the container C may be about −3 degrees Celsius so that, for instance, testing of the container C may begin at about 0 degrees Celsius.

With reference to FIGS. 3 and 4, the utility bay 28 may carry a computer subsystem, which may include a controller

40 and a graphical user interface 42 coupled to the controller 40. The controller 40 may include, for example, a National Instruments (NI) cRIO-9075 controller, or any other suitable device(s). The interface 42 may include, for instance, an APC 18W5 touch panel computer, or any other suitable device(s). The bay 28 also may include any other suitable utilities for carrying out container testing. For example, the bay 28 may include one or more metering pumps 44, for instance, a peristaltic pump, which may be a computer-compatible/programmable digital drive pump, for instance, a Masterflex L/S 07551-00 pump. Also, the bay 28 may include one or more stirring pumps 46, for instance, a Hagen AquaClear 5 pump. Further, although not separately shown, the bay 28 may include sensor interfaces, for instance, an NI USB 9213 interface, and a digital to analog converter, for instance, a NI 9403 module. Further, as shown in FIG. 3, the utility bay 28 may include one or more exhaust fans 48, which may be carried by a panel 30 corresponding to the bay 28.

As shown in FIG. 4, the bay 28 may include interior panels 36 and shelves 34 with ventilation apertures 38 therethrough. More specifically, a vertical panel 36 may include a ventilation aperture 38 in communication between the test assembly bay 24 and the utility bay 28, and a horizontal panel or shelf 34 may include a ventilation aperture 38 in communication between the cooler bay 26 and the utility bay 28. Accordingly, the exhaust fans 48 may operate to pull cooler air from the test bay 24 and/or the cooler bay 26, through the utility bay 28, and out of the utility bay 28 to the exterior of the system 10.

Figure 5:
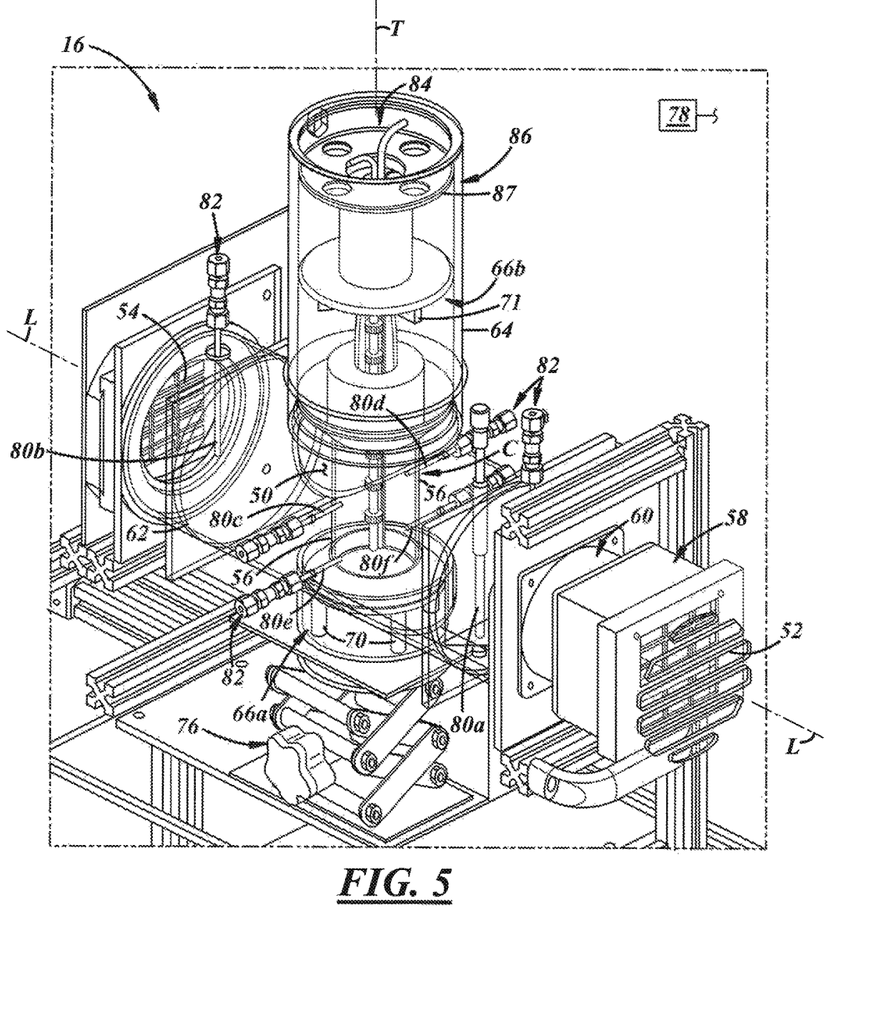
FIG. 5 is an enlarged, fragmentary, perspective view of a test chamber of the test stand of FIG. 1.

With reference to FIG. 5, the test assembly 16 may include a test chamber 50 including an air inlet 52, an air outlet 54 downstream of the air inlet 52, and a container location 56 between the inlet 52 and the outlet 54. The test assembly 16 further may include a fan 58 to generate airflow between the upstream inlet 52 and the downstream outlet 54, and/or one or more climate controllers 60 to control the climate in the test chamber 50. For example, the climate controller(s) 60 may be located upstream of the container location 56 and may heat and/or cool air. The fan 58 may be located at an upstream end of the test chamber 50, for example, as shown in the drawings, upstream of the climate controller(s) 60. In other embodiments the fan 58 may be located at a downstream end of the test chamber 50 or anywhere midstream between the upstream and downstream ends. Any suitable fan may be used, and the fan 58 may be powered by a BK Precision 1696 power supply, and fan speed may be monitored via a Newport P6001A frequency meter. The climate controller(s) 60 may include a heater, for example, a KLC Corporation MSH-1120-70S heater, or any other suitable heater. In other embodiments, the climate controller(s) 60 also or instead may include a chiller, vortex cooler, or any suitable refrigeration apparatus. The fan 58 and climate controller(s) 60 may be powered via any suitable power distributors, relays, and/or the like, which may be located in the test bay 24 and/or the utility bay 28 (FIG. 1). In other embodiments, although not illustrated, the climate controller(s) 60 instead may include portions in direct contact with the container C, for example, resistive heaters or the like.

Figures 6, 7, 8:
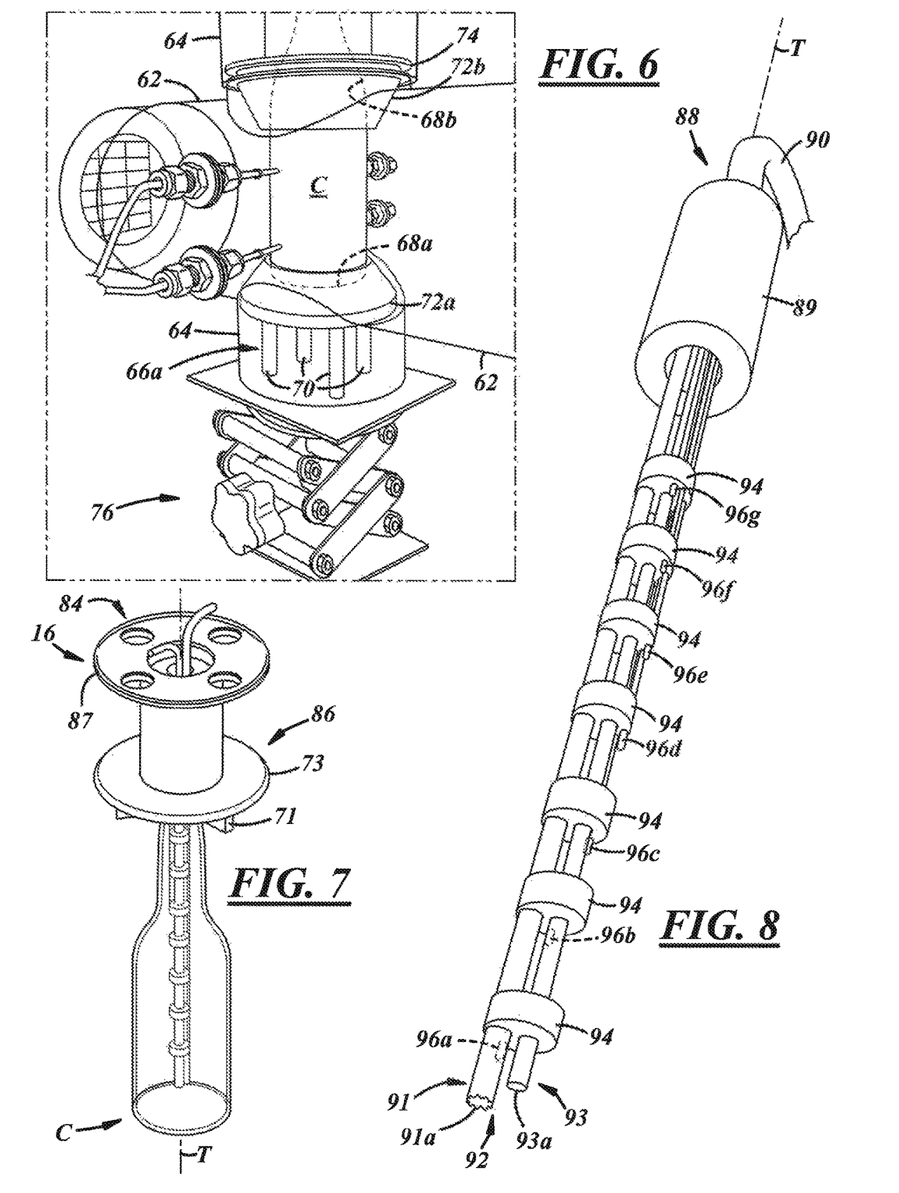
FIG. 6 is an enlarged, fragmentary, perspective view of the test chamber shown in FIG. 5.
FIG. 7 is an enlarged perspective view of a container and a probe head assembly coupled to the container.
FIG. 8 is an enlarged perspective view of a utility wand of the probe head assembly of FIG. 7.

Also, with reference to FIGS. 5 and 6, the test chamber 50 may include an airflow conduit 62 between the upstream inlet 52 and the downstream outlet 54 to convey air to, around, and past the container location 56. Likewise, a container conduit 64 may intersect the airflow conduit 62 between the upstream inlet 52 and the downstream outlet 54 and may carry the container C therein at the container location 56. The conduits 62, 64 may include tubing, pipe, or the like, which may be composed of glass, plastic, or any other suitable material and may be cylindrical or of any other suitable shape. The conduits 62, 64 may be translucent, preferably, transparent, as illustrated to facilitate viewing of container testing. The conduits 62, 64 may be sealed to one another and, for example, may be welded, adhered, fastened, or otherwise coupled together to provide the test chamber 50 in a sealed configuration.

With reference to FIG. 6, the test assembly 16 also may include one or more locators 66a,b and, for example, may include multiple sets of first and second locators for different container sizes. For instance, the assembly 16 may include a first locator 66a to locate a base of the container C in the test chamber 50, and a second locator 66b to locate another portion of the container C in the chamber 50. For example, the locator 66b may locate a shoulder and/or one or more other portions of the container C, for instance, a neck portion and/or a body portion. The first locator 66a may include one or more feet 70 and a perforated plate (not separately shown) from which the feet 70 may extend. Likewise, the second locator 66b may include circumferentially spaced, radially extending locator ribs 71 that may be carried on an undersurface of a plate 73 for radial engagement with an exterior surface, for example, of a neck finish, of the container C.

Additionally, lower and upper frustoconical bodies 72a, 72b may disposed around portions of the container C, for example, to serve as masks to deflect airflow and selectively confine exposure of only desired portions of the exterior surface of the container C to the heated air. For instance, this arrangement may replicate heat transfer from a consumer's hand grip on a body portion of the container C. The frustoconical bodies 72a, 72b may be puck-like components having exterior surfaces corresponding to interior surfaces of the conduit 64, and hollow interiors for contacting the container C. An interior 68a of one of the bodies 72a may be a pocket and an interior 68b of another one of the bodies 72b may be a through passage. The upper frustoconical body 72b may include a seal groove 74 for carrying a seal (not shown) for sealed coupling to the conduit 64. Similarly, the lower frustoconical body 72a may include a seal groove and seal (not shown). The locators 66a,b and bodies 72a,b may be replaced by larger or smaller locators and bodies to accommodate larger or smaller containers.

With reference to FIGS. 5 and 6, the system 10 also may include a positioning stage 76 to position the container C with respect to the test chamber 50. The stage 76 may include a manual screw jack, for example, as illustrated, a servo ball screw, or any other suitable positioning stage to move the container C. The feet 70 of the first locator 66a may rest on top of the stage 76. Accordingly, smaller and larger sized containers may be accommodated.

With reference to FIG. 5, the test assembly 16 also may include one or more air temperature sensors, for example, in a sensor array. An ambient air temperature sensor 78 may be located in any suitable location in the test bay 24. The sensors also may include, for example, at least one upstream temperature sensor 80a upstream of the container location 56, at least one downstream temperature sensor 80b downstream of the container location 56, and one or more midstream temperature sensors 80c-f, adjacent to the container location 56 between the upstream and downstream temperature sensors 80a,b. The upstream temperature sensor 80a may be located between the container location 56 and the inlet 52. The downstream temperature sensor 80b may be located between the container location 56 and the outlet 54.

The midstream temperature sensors 80c-f may include one or more temperature sensors on opposite sides of the test chamber. For example, one or more upper sensors 80c and/or 80d and one or more lower sensors 80e and/or 80f may be located on opposite sides of the container location 56. The upstream and downstream temperature sensors 80a,b may include probes or other portions that extend into the test chamber 50 and that also may extend across a central longitudinal axis L of the chamber 50. The midstream temperature sensors 80c-f may include probes or other portions that extend into the test chamber 50 and to a position configured to be adjacent an exterior surface of the container C. For example, free ends of sensor probes may terminate within five millimeters (mm) from the exterior surface of the container C and, more specifically, within 2 mm thereof but not touching the container C. As illustrated, the sensors 80a-f may include adjustment couplings 82 to allow the sensors 80a-f to be advanced and retracted to desired positions in the test chamber 50. The couplings 82 may include mechanical sub-assemblies that, when adjusted, compress an outer sheath of the sensors 80a-f, locking the sensors 80a-f in their intended positions relative to the container C. In any case, the sensors 80a-f may extend through corresponding apertures of the conduit 62.

With reference to FIG. 7, the test assembly 16 also may include a test probe head 84 for coupling to the container C and providing fluid flow to and from the container C and for obtaining temperatures in the interior of the container C. The test probe head 84 may include a probe head locator 86 to locate other portions of the test probe head 84 with respect to other portions of the test assembly 16 and/or the container C. The probe head locator 86 may include a puck-like component having a radially outermost exterior 87 to contact a corresponding portion of the test assembly 16, for example, the inside of the container conduit 64 (FIG. 5). The probe head locator 86 also may include a through passage that may extend along a transverse axis T for carrying other portions of the test probe head 84.

For example, and with reference to FIG. 8, the test probe head 84 may locate and retain a test probe assembly 88, which may include a handle 89 coupling to a utility conduit 90 and having a through passage for communicating various utility components therethrough. For example, the utility conduit 90 may include any suitable tube(s), hose(s), cable (s), wire(s), and/or the like. The probe assembly 88 also may include at least one fluid conduit 92 extending through and carried by the handle 89, at least one means of stirring the fluid contents, a plurality of axially spaced supports 94 coupled to the conduit 92, and a plurality of liquid temperature sensors 96a-g.

The temperature sensors 96a-g may be arranged in a circumferentially and axially spaced array. For example, the sensors 96a-g include axial ends or sensing portions located at a plurality of different levels spaced axially and circumferentially apart from one another, and that may correspond to each of the supports 94. More specifically, the sensing portions may be spaced about one inch intervals, plus or minus half an inch. In the illustrated example, the sensing portions may extend past respective supports for up to a few millimeters. Accordingly, the sensors 96a-f may be circumferentially and axially spaced about the probe assembly 88, for example, about the transverse axis T. The sensors 96a-g may include 30AWG wires carried by probe tubes that may be carried by the supports 94.

The fluid conduit 92 may include a liquid delivery and extraction conduit 91, and may include a separate liquid agitation conduit 93. The liquid delivery and extraction conduit 91 may include a serrated or otherwise relieved end 91a to facilitate extraction, and the liquid agitation conduit 93 may include an end 93a that is spaced axially shy of the end 91a of the other conduit 91. In other embodiments, the conduits 91, 93 may be a single, unitary conduit coupled to any suitable upstream valves, conduit, pumps, and/or the like.

A method of assessing insulative properties of a container may include the following steps, with general reference to the drawing figures as just one of many possible examples of systems to carry out the method.

A container may be positioned in a test chamber. For example, the container C of FIG. 5 may be positioned in the test chamber 50 of FIG. 5. More specifically, the access panel 31 (FIG. 1) may be removed and the container C inserted into an open end of the container conduit 64 (FIG. 5) and located therein using the locators 66a,b. Moreover, the probe head 84 may be lowered into the container conduit 64 so that the test probe assembly 88 (FIG. 8) locates within the container C, but the conduit 92 and the sensors 96a-g do not contact the inside surfaces of the container C.

Thereafter, the container C may be thermally preconditioned, or thermally soaked. In one embodiment, the climate controller(s) 60 may precondition the container C, for example, by providing the test chamber with cold air, for instance, between 30° C. and 35° C. This embodiment may be used alone or in addition to the embodiment described hereafter. In another embodiment, cooled liquid may be cycled through the container C to at least one level. The cycling may include delivering the cooled liquid from the source 14 of the cooled liquid to the at least one level inside of the container C, waiting for a period of time, and then extracting the liquid from the inside of the container C. For example, the cooled liquid may be delivered from the cooled liquid source 14 by the liquid pump 44, through the test probe head 84 and the test probe assembly 88, and into the container C. The period of time may be, for example, between 0.001 and 180 seconds, including any ranges and sub-ranges therebetween. The liquid may be extracted by the liquid pump 44 from inside the container C, through the test probe assembly 88 and test probe head 84, and to a system drain chamber or external waste drain (not shown). The preconditioning step may include any suitable quantity of cycles, for instance, in correspondence to the quantity (n) of the liquid temperature sensors 96a-g. For example, the preconditioning cycles may include n, n–1, or any other suitable quantity of cycles. Alternatively, the number of cycles may be two, three, or any other suitable quantity, for instance, where the difference in liquid temperature in the container C from cycle to cycle falls below some predetermined acceptable value (e.g., about 3° C.) sufficient to begin testing.

Subsequently, the container C may be filled with cooled liquid by delivering the cooled liquid from the cooled liquid source 14 until the cooled liquid reaches a fill level in the container C. For example, the liquid pump 44 may deliver the cooled liquid from the source 14 to the container C until the cooled liquid reaches a fill capacity for the container C. For example, if the container is a 12 oz. bottle, then the fill capacity may be 12 ounces, plus or minus production tolerances well known to those of ordinary skill in the art.

At any suitable time, the outside of the container C may be thermally treated, for example, by using the climate controller(s) 60 to control the climate in the chamber. For example, heat or cold may be applied continuously, or progressively, for instance, in a periodic step-wise manner. For example, in the illustrated embodiment, this step may include thermally treating air with the climate controller(s) 60 and flowing the air past the climate controller(s) 60 and toward the container C. More specifically, the climate controller(s) 60 may be activated and the fan 58 may be activated to move heated air through the test chamber 50. In other examples, any other suitable heating techniques may be used, including using induction heating, laser heating, or any other suitable manner of heating the outside of the container C.

Further, at any suitable time, temperature of the air outside the container C may be measured. This step may include measuring a plurality of temperatures of the air, including an upstream air temperature, a downstream air temperature, and/or a midstream air temperature proximate the container. For example, one or more of the air temperature sensors 80*a-f* in the test chamber 50 may be monitored by the computer sub-system to measure the air temperature.

Also, at any suitable time, temperature of the liquid inside the container C may be measured. This step may include measuring a plurality of temperatures of the liquid at different levels within the container C. For example, the temperature sensors 96*a-g* of the probe assembly 88 may be monitored by the computer sub-system to measure the liquid temperature. The temperature may be measured during the preconditioning step, for instance, for use as fill level indicators. More specifically, levels of liquid inside the container C, for example, at each of the supports 94, can be determined using the corresponding temperature sensors 96*a-g* corresponding to each of those supports 94. Each of the corresponding temperature sensors 96*a-g* may report its temperature at intervals greater than or equal to 0.001 seconds, creating a real-time reporting of the temperature at that sensor location.

The fill level of the container C may be determined via other embodiments. For example, the uppermost temperature sensor 96*g* may be a fill level switch instead of a temperature sensor. In another embodiment, a fill level of the container C may be determined by weight, via one or more load cells (not shown) that may be disposed beneath the container C in any suitable manner and communicated in any suitable manner to the controller 40. In yet another embodiment, a flow meter (not shown) may be in fluid communication between the pump(s) 44 and the container C and communicated in any suitable manner to the controller 40.

The liquid temperature measurements may be plotted and output to the user interface 42 at any suitable time intervals after the test is initiated, for example, at 6, 7, 8, 9, etc. minutes after a test cycle is initiated. Accordingly, plots taken from testing of different containers of various geometries and compositions can be compared and contrasted to assess relative insulative performance of the different containers. The plots may demonstrate changes in temperature over changes in time. The containers may be tested with or without labels or other elements carried by the containers.

One or more additional steps may be provided to simulate consumption of the liquid by a consumer. For example, the method further may include the step of extracting liquid from the container C while continuing to measure temperature of the liquid in the container C. The liquid may be extracted continuously, or progressively, for instance, in a periodic step-wise manner. Also, the method may include the step of agitating the liquid in the container C, at any suitable time. The agitation of the liquid within the container may occur continuously, or progressively, for instance, in a periodic step-wise manner. For instance, the air pump 46 may blow air into the container C via the liquid agitation conduit 93 of the test probe assembly 88 and test probe head 84, for example, during the preconditioning step and/or during the steps of measuring the liquid temperature and/or extracting the liquid. Blowing air into the liquid in the container C may be used to generate bubbles and stir the liquid in the container C, thus homogenizing the liquid temperature in the container C because liquid temperatures within the container C may separate at varying levels.

In general, the computer sub-system mentioned above may be used to carry out various aspects of the presently disclosed method. In one example, the computer sub-system may receive input data and instructions from a user, process the received input in light of stored software and/or data, and transmit output signals to the climate controller, fan(s), pumps, and any other suitable portions of the system 10. Conversely, in another example, the computer sub-system may receive input signals from the air temperature sensors 78, 80*a-f*, the climate controller(s) 60, the fan 58, the pumps 44, 46, and any other suitable portions of the system 10, process the received input signals in light of stored data and software, and transmit output data to the user, for example, via the interface 42.

Although not separately illustrated, the computer sub-system generally may include memory, a processor coupled to the memory, one or more interfaces coupled to the processor, one or more input devices coupled to the processor, and/or one or more output devices coupled to the processor. Of course, the computer sub-system further may include any ancillary devices, for example, clocks, internal power supplies, and the like (not shown). Although not shown, the computer sub-system may be supplied with electricity by an external power supply, for example, an AC to DC transformer, one or more batteries, fuel cells, and the like.

The various input devices and output devices may be separate or integrated, and may be used to receive or transmit any suitable user input or output, whether tactile, audible, and/or visual. The input devices may include peripheral input devices or user input devices, for example, a pointing device (e.g., a mouse, trackball, pen, touch pad, touch screen, joystick, and the like), keyboard, microphone, camera, and/or the like. The input devices may be used to communicate any suitable commands, instructions, data, information, signals, and the like into the processor. The output devices may include user output devices, for example, audio speakers or earphones, or a monitor or any other type of display device, or may include peripheral output devices, for example, a printer, a modem or any other communication adapter, and/or the like.

The interfaces may include internal and/or external communication interfaces and may include wired and/or wireless devices. For example, the interfaces may include an internal bus, which may provide for data communication between the processor, memory, and/or other interface elements of the computer sub-system. In another example, the interfaces may include an external bus for data communication between elements of the computer sub-system and peripheral devices. The interfaces may include one or more of any of several types of bus structures, including a memory bus or memory controller, a peripheral bus, an accelerated graphics port, a local or processor bus, and using any of a variety of bus architectures. Also, the interfaces may include analog-to-digital or digital-to-analog converters, signal conditioners, amplifiers, filters, other electronic devices or software modules, and/or any other suitable interfaces. The interfaces may conform to, for example, RS-232, parallel, small computer system interface, universal serial bus, and/or any other suitable protocol(s). The interfaces may include circuits, software, firmware, and/or any other device to assist or enable the computer sub-system in communicating internally and/or externally with other devices.

The processor may process data and execute instructions that provide at least some of the functionality for the test system. As used herein, the term instructions may include, for example, control logic, computer software and/or firmware, programmable instructions, or other suitable instructions. The processor may include, for example, one or more microprocessors, microcontrollers, discrete logic circuits having logic gates for implementing logic functions on data signals, application specific integrated circuits with suitable logic gates, programmable or complex programmable logic devices, programmable or field programmable gate arrays, and/or any other suitable type of electronic processing device(s).

The memory may include any computer readable medium or media configured to provide at least temporary storage of at least some data, data structures, an operating system, application programs, program modules or data, and/or other computer software or computer-readable instructions that provide at least some of the functionality of the system and that may be executed by the processor. The data, instructions, and the like may be stored, for example, as look-up tables, formulas, algorithms, maps, models, and/or any other suitable format. The memory may be in the form of removable and/or non-removable, volatile memory and/or non-volatile memory. Illustrative volatile memory may include, for example, random access memory (RAM), static RAM (SRAM), dynamic RAM (DRAM) including synchronous or asynchronous DRAM, and/or the like, for running software and data on the processor. By way of example, and not limitation, the volatile memory may include an operating system, application programs, other memory modules, and data. Illustrative non-volatile memory may include, for example, read only memory (ROM), erasable programmable ROM (EPROM), electrically erasable programmable ROM (EEPROM), dynamic read/write memory like magnetic or optical disks or tapes, and static read/write memory like flash memory, for storing software and data. Although not separately shown, the computer sub-system may also include other removable/non-removable volatile/non-volatile data storage or media. For example, the other media may include dynamic or static external storage read/write device(s)

The methods or parts thereof can be implemented in a computer program product including instructions carried on a computer readable medium for use by one or more processors of one or more computers to implement one or more of the method steps. The computer program product may include one or more software programs comprised of program instructions in source code, object code, executable code or other formats; one or more firmware programs; or hardware description language (HDL) files; and any program related data. The data may include data structures, look-up tables, or data in any other suitable format. The program instructions may include program modules, routines, programs, objects, components, and/or the like. The computer program product can be executed on one computer or on multiple computers in communication with one another.

The program(s) can be embodied on non-transitory computer readable media, which can include one or more storage devices, articles of manufacture, or the like. Example non-transitory computer readable media include computer system memory, e.g. RAM (random access memory), ROM (read only memory); semiconductor memory, e.g. EPROM (erasable, programmable ROM), EEPROM (electrically erasable, programmable ROM), flash memory; magnetic or optical disks or tapes; and/or the like. The non-transitory computer readable medium may also include computer to computer connections, for example, via a network or another communications connection (either wired, wireless, or a combination thereof). Non-transitory computer readable media include all computer readable media, with the sole exception of transitory propagating signals. Any combination(s) of the above examples is also included within the scope of the computer-readable media. It is therefore to be understood that the method(s) can be at least partially performed by any electronic articles and/or devices capable of executing instructions corresponding to one or more steps of the disclosed method(s).

It is therefore to be understood that the method may be at least partially performed by any electronic articles and/or devices capable of executing instructions corresponding to one or more steps of the disclosed method.

There thus has been disclosed a container test system for, and a method of, assessing insulative performance of a container, that fully satisfies one or more of the objects and aims previously set forth. The disclosure has been presented in conjunction with several illustrative embodiments, and additional modifications and variations have been discussed. Other modifications and variations readily will suggest themselves to persons of ordinary skill in the art in view of the foregoing discussion. For example, the subject matter of each of the embodiments is hereby incorporated by reference into each of the other embodiments, for expedience. The disclosure is intended to embrace all such modifications and variations as fall within the spirit and broad scope of the appended claims.

The invention claimed is:

1. A container thermal property test system that includes:
a test chamber including an air inlet, an air outlet downstream of the air inlet, and a container location between the air inlet and the air outlet;
a climate controller located upstream of the air outlet, to control the climate in the test chamber;
a computer sub-system;
at least one air temperature sensor located adjacent to the container location to sense air temperature in the test chamber between the air inlet and the air outlet for monitoring by the computer sub-system to measure air temperature; and
a test probe assembly to extend into the test chamber in the container location between the air inlet and the air outlet and including a plurality of liquid temperature sensors for monitoring by the computer sub-system.

2. The system set forth in claim 1 that also includes: a plurality of air temperature sensors, including: an upstream air temperature sensor upstream of the container location; a downstream air temperature sensor downstream of the container location; and the at least one air temperature sensor between the upstream and downstream air temperature sensors.

3. The system set forth in claim 1 that also includes a fan to generate airflow between the upstream inlet and the downstream outlet.

4. The system set forth in claim 1 wherein the climate controller includes a heater to heat air upstream of the container location.

5. The system set forth in claim 1 wherein the at least one air temperature sensor includes two or more air temperature sensors on opposite sides of the test chamber.

6. The system set forth in claim 5 wherein the at least two air temperature sensors include two or more pairs of upper and lower air temperature sensors.

7. The system set forth in claim 1 wherein the plurality of liquid temperature sensors are disposed at a plurality of different levels spaced apart from one another.

8. The system set forth in claim 1 that includes the test probe assembly including a liquid delivery and extraction conduit to deliver and extract liquid with respect to the container location.

9. The system set forth in claim 1 that includes the test probe assembly including a liquid agitation conduit to agitate liquid in the container location.

10. The system set forth in claim 1 that includes the test probe assembly extendable into the test chamber and including a plurality of axially spaced supports, a plurality of liquid temperature sensors for monitoring by the computer sub-system and carried by the plurality of supports and axially and circumferentially spaced apart from one another, and a liquid delivery and extraction conduit carried by the plurality of supports.

11. The system of claim 1, further including a container at the container location, wherein the test probe assembly extends into the container at the container location.

12. A container test system that includes:
a test chamber including:
an air inlet;
an air outlet downstream of the air inlet;
a container location between the air inlet and the air outlet;
an airflow conduit between the air inlet and the air outlet to convey air to, around, and past the container; and
a container conduit intersecting the airflow conduit between the air inlet and the air outlet;
a climate controller located upstream of the air outlet, to control the climate in the test chamber;
at least one air temperature sensor located adjacent to the container location to sense air temperature in the test chamber between the air inlet and the air outlet; and
a test probe assembly to extend into the test chamber in the container location between the air inlet and the air outlet and including a plurality of liquid temperature sensors.

13. The system set forth in claim 12 wherein the system includes:
a first locator to locate a base of the container in the test chamber; and
a second locator to locate one or more other portions of the container in the container conduit.

14. The system set forth in claim 13 wherein the system includes a positioning stage to position a container with respect to the test chamber.

15. The system of claim 12, wherein the intersecting airflow and container conduit includes at least one of intersecting tubing or intersecting piping.

16. The system of claim 12, wherein the intersecting airflow and container conduit is at least translucent.

17. A method of processing a container that includes the steps of: positioning the container in a test chamber; filling the container with liquid by delivering the liquid from a liquid source until the liquid reaches a fill level in the container; thermally treating an outside of the container within the test chamber; measuring temperature of air in the test chamber outside the container with at least one air temperature sensor; and measuring temperature of the liquid inside the container with at least one liquid temperature sensor.

18. The method set forth in claim 17 that also includes thermally preconditioning the container.

19. The method set forth in claim 18 that also includes the steps of:
providing liquid at a source of liquid;
cooling the liquid;
wherein the thermally preconditioning step includes cycling the liquid through the container to at least one level including:
delivering the liquid from the source of the liquid to the at least one level inside of the container,
waiting for a period of time, and then
extracting the liquid from the inside of the container.

20. The method set forth in claim 19 wherein the preconditioning step includes at least one additional step of cycling liquid to at least one additional level within the container.

21. The method set forth in claim 19 that also includes the step of agitating the liquid in the container.

22. The method set forth in claim 14 that also includes the step of continuously or progressively extracting liquid from the container while continuing to measure temperature of the liquid in the container.

23. The method set forth in claim 17 wherein the thermal treating step includes flowing heated air past the container by heating air with a heater and moving air past the heater and toward the container.

24. The method set forth in claim 17 wherein the step of measuring temperature of the liquid includes measuring a plurality of temperatures of the liquid at different levels within the container.

25. The method set forth in claim 17 wherein the step of measuring temperature of the air includes measuring a plurality of temperatures of the air, including an upstream air temperature, a downstream air temperature, and a midstream air temperature proximate the container.

26. A computer program product stored on a computer-readable storage medium and including instructions executable by a computer processor of a container test system to cause the system to implement steps of a method according to claim 17.

27. A computer-controlled system, comprising:
a memory storing program instructions; and
a processor coupled to the temperature sensor(s) and memory and responsive to the program instructions for causing the computer-controlled system to perform a method according to claim 17.

* * * * *